United States Patent [19]

Vijg et al.

[11] Patent Number: 5,068,176

[45] Date of Patent: Nov. 26, 1991

[54] METHOD FOR THE SIMULTANEOUS DETERMINATION OF DNA SEQUENCE VARIATIONS AT A LARGE NUMBER OF SITES, AND A KIT SUITABLE THEREFOR

[75] Inventors: Jan Vijg; Andreas G. Uitterlinden, both of Rotterdam, Netherlands

[73] Assignee: Nederlandse Organisatie voor toegepastnatuurwetenschappelijk onderzoek TNO, Gravenhage, Netherlands

[21] Appl. No.: 345,887

[22] Filed: May 1, 1989

[30] Foreign Application Priority Data

May 2, 1988 [NL] Netherlands .......................... 8801147

[51] Int. Cl.$^5$ ...................... C12Q 1/68; C07H 15/12; G01N 33/566; C12N 15/00
[52] U.S. Cl. ......................................... 435/6; 435/810; 536/27; 935/77; 935/78; 436/501; 436/808
[58] Field of Search ...................... 435/6, 810; 536/27; 935/77, 78; 436/501, 808

[56] References Cited

PUBLICATIONS

Fischer et al (1979), Cell 16, 191–200.
Southern (1975), J. Mol. Biol. 98, 503–517.

*Primary Examiner*—Robert A. Wax
*Assistant Examiner*—Mindy B. Fleisher

[57] ABSTRACT

This invention relates to a method of simultaneously determining DNA sequence variations on a large number of loci, and a kit suitable therefor. The method comprises an electrophoretic separation of restriction fragments in two dimensions on the basis of two independent criterions, namely, length and base pair sequence, and a detection of separated fragments by means of a labelled probe comprising one or more units of minisatellite sequences. Preferred probes are GC-rich minisatellite core sequences.

9 Claims, 9 Drawing Sheets

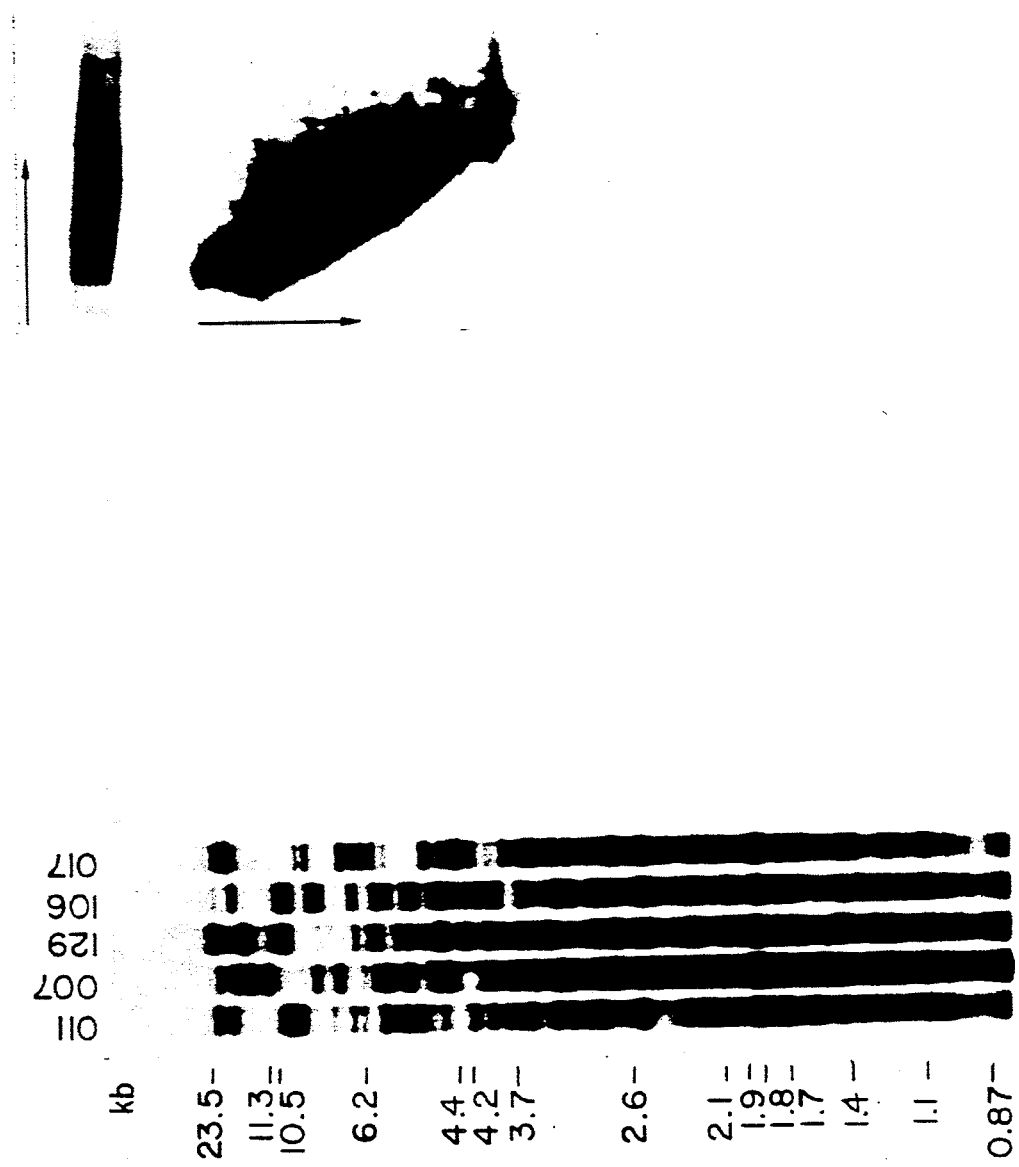

ELECTROPHORESIS

VNTR CORE SEQUENCES

| probe | sequence | origin |
|---|---|---|
| 33.6 | GGAGGCTGGAGGAG | Hu-myoglobin |
| 33.15 | GGAGGTGGGCAGGAAG | Hu-myoglobin |
| INS | ACAGGGGTGTGGGG | Hu-insulin |
| alpha | AACAGCGACACGGGGGG | Hu-alphaglobin |
| Zèta | TGGGGCACAGGCTGTGAG | Hu-zètaglobin |
| Hras | GGGGGAGTGTGGCGTCCCT GGAGAGAA | Hu-cHa-ras I oncogene |
| HBV | GGAGTTGGGGGAGGAG | viral |
| M13 | GAGGGTGGCGGCTCT | viral |

FIG. 7A

VNTR CORE PROBE PREPARATION

I. oligo synthesis

A core sequence →
B complementary and partially overlapping sequence →

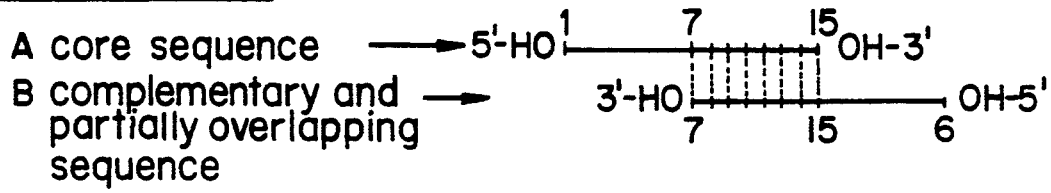

II. polymerization 1 kinase A and B oligo's
2 anneal at 42°C:

3 ligate:

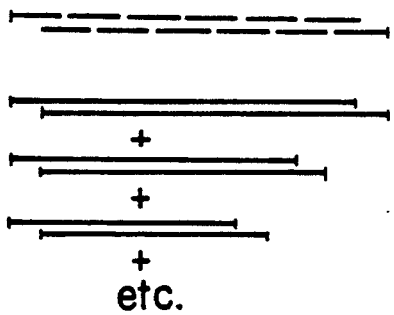

III. self-prime labelling 1 denature by boiling
2 incubate +dNTP's +α$^{32}$P-dCTP-Klenow enzyme

FIG. 7B

PAA GELELECTROPHORESIS OF VNTR CORE POLYMER PROBES

6% PAAGE

1 + 7 = ØxHae III marker
2 = INS
3 = 33.15
4 = HBV
5 = 33.15
6 = Zèta

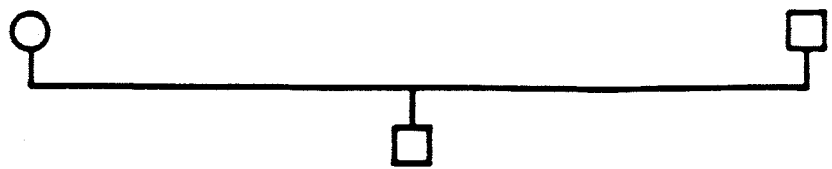
FIG.IOD
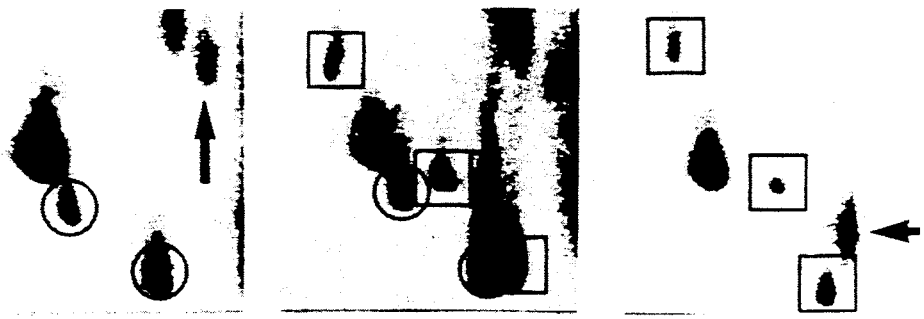
FIG.IOA
FIG.IOB
PROBE 33.6
FIG.IOC

METHOD FOR THE SIMULTANEOUS DETERMINATION OF DNA SEQUENCE VARIATIONS AT A LARGE NUMBER OF SITES, AND A KIT SUITABLE THEREFOR

This invention relates to a method of detecting genetic variation by fragmenting double-stranded DNA of an individual by means of one or more restriction enzymes, separating the resulting fragments in 2 dimensions by electrophoresis, transferring the resulting separation pattern to a membrane filter, hybridizing thereon with a labelled DNA or RNA probe under DNA-denaturing conditions, and visualizing the label.

Such a method is in the field of so-called DNA diagnostics, i.e., the use of methods of analysis for demonstrating genetic variation which may be an indication for contracting diseases, exposure to carcinogenics, etc., and can serve for the identification of an individual. Genetic variation generally means differences between individuals as regards the base sequence of their DNA. Genetic variation can be detected by means of hybridization analysis after electrophoretic separation of DNA fragments, generated by digestion with a restriction enzyme (Southern Blot hybridization analysis; Southern, 1975). Hybridization with a specific radioactively labelled DNA fragment (probe) results, after autoradiography, in one or more select bands. Each band represents a DNA fragment hybridized with the probe used. The position of the bands is a measure for the size of the fragments in question. If, for one specific probe, the position of the bands varies between individuals, as a result of deletions/inserts and/or the presence or absence of the recognition site for the restriction enzyme used, this is called genetic polymorphism, or restriction fragment length polymorphism. Experience has taught that some regions in the genome exhibit more polymorphism than others. Probes for such polymorphic regions are extremely useful, because within a family in which an heritable disease occurs, the inheritance of this disease, together with a variant of the polymorphous DNA sequence in question indicates that the defect gene is in close proximity thereto (for a survey, see Gusella, 1986). This is called the genetic "mapping" of disease genes. Naturally it is then of great importance to know precisely where the polymorphous marker sequences are located, both relatively to each other and on a particular chromosome. Ultimately the entire genome can be mapped in this manner by determining the relative positions of a large number of polymorphic markers (linking them together, so to say) (for a survey, see Botstein et al., 1984). Recently, provisional linkage maps of parts of) the human genome have been made on the basis of hundreds more or less polymorphic markers (Donis-Keller et al., 1987, Nakamura et al., 1988). By means of such genetic maps of the human genome, each inheritable disease can in principle be linked to a specific locus in the genome. Depending on the accuracy of the localization (and hence on the informativeness of the linkage map) the disease gene itself could then ultimately be isolated.

The prior art linkage maps, however, have a number of disadvantages. First not all markers are equally informative, i.e. polymorphic. This means that there is a great chance that in a family with the heritable disease one wishes to study, each individual has the same variant of the marker. In that case, therefore, no segregation of healthy and defective alleles can be observed. Furthermore, not all markers are uniformly distributed over the genome.

A potential alternative for generating a linkage map is the use of so-called hyperpolymorphic minisatellites, also termed VNTR (Variable Number of Tandem Repeat) sequences. Minisatellite sequences (Jeffreys 1985a) are so-called tandem repeat sequences. Interindividual variation in the number of repetitive units makes them extremely polymorphic (see FIG. 1). Many minisatellites are extremely informative (hyperpolymorphic) and occur on all chromosomes (see FIG. 2). Indeed, it has been proposed (Nakamura et al., 1987) to isolate locus-specific minisatellite probes on a large scale and to use them as markers for an (extremely informative) genetic linkage map.

As soon as a set of hyperpolymorphic markers, proportionately distributed over the genome, is available, any heritable disease can in principle be mapped. However, to accomplish this, a great many experiments are needed as a result of the relatively low resolution of the method of separation used. In fact, when the locus-specific minisatellites are used, no more than 2 alleles (1 locus) per individual can be scored. Although, in principle, it is possible to visualize a great many, if not all, minisatellites in an experiment by means of a minisatellite core sequence, this is an endless task for linkage analysis by means of Southern analysis. FIG. 3 shows that, if use is made of a minisatellite core sequence as the DNA probe, a great many fragments are detected. However, only about 15 of the largest bands can be observed separate from each other. Each band represents one allele (assuming that the restriction enzyme used does not cut the minisatellite). The resulting banding is different for each individual, which can be used for identification purposes (Jeffreys, 1985b; EP-A-0186271). However, as so few loci can be analyzed simultaneously, and as it is never guaranteed that both alleles (both the paternal and the maternal one) of a given locus can be demonstrated at the same time, the use of this system for linkage analysis is barred.

The proposal (Nakamura et al., 1987) to use minisatellite probes for generating a so-called linkage map, i.e. mapping the human genome, is limited to the use of locus-specific probes, so that their repetitive character cannot be utilized. For linkage analysis, the core sequence, which shows the sum of all minisatellite containing loci belonging to that family, cannot be used, but each locus must be analyzed separately by means of a cloned allele as a probe. Repeat sequences, even if they are polymorphic, are generally unsuitable for linkage analysis, because the low resolution of one-dimensional Southern blot analysis does not permit visualizing all alleles of a repeat sequence family separate from each other on one autoradiogram.

As indicated above, genetic variation has hitherto virtually exclusively been demonstrated by means of the well-known Southern blot hybridization analysis (Southern, 1975). By means of this, a large number of variation points have been detected, some of which have a direct medical significance, such as certain variations in the genes for globin, which are responsible for a number of diseases (for a survey, see Gusella, 1986), and others are otherwise interesting because they can be used to perform identity testing, such as the above-described minisatellites (Jeffreys, 1985b; EP-A-0186271).

By the end of the seventies, an alternative method of separation has been developed, which is based on the melting-out behaviour of a DNA fragment (Fischer and Lerman, 1979). If two DNA fragments of identical length, but different as regards their base pair composition migrate, under the influence of an electric field, through a polyacrylamide gel in which a gradient of denaturant (e.g. urea/formamide) or a temperature gradient (see, e.g., Po et al., 1987) has been provided, they will melt at a specific point. This point in the gradient is highly sequence-dependent, so much so that, if the two fragments differ at one site only, this already results in a difference in melting-out behaviour. Melting takes place abruptly at a given concentration of denaturant and results in a great delay in migration. This separation of DNA fragments on the basis of their base pair sequence is independent of their size.

In the article referred to (Fischer and Lerman, 1979), this separation criterion is combined with size separation in order to generate a two-dimensional pattern. This system, which owing to its two different separation criteria differs from other 2-dimensional DNA separation systems, was used with the DNA of the bacterium *Escherichia coli* to separate fragments obtained by digestion with the restriction enzyme EcoRI. After electrophoretic separation, the DNA fragments were visualized by staining with ethidium bromide. Compared with the human genome, which contains about $3 \times 10^9$ base pairs, *E.coli* is an organism with an extremely simple DNA, which after digestion with a restriction enzyme can be fully resolved on such a 2-dimensional gel. Hitherto, 2-dimensional gels in accordance with the above principle have not been used in the analysis of the human genome. Naturally, the great complexity of the human genome bars a 2-dimensional analysis of total genomic DNA on the basis of staining with ethidium bromide; the number of fragments to be expected (one million after digestion with EcoRI) is simply too large.

This problem could possibly be overcome if, in analogy with the well-known Southern blot hybridization analysis, the separation pattern could be transferred, for example, to nitrocellulose paper, followed by hybridization with one or more suitable probes.

Practice has shown, however, that the transfer of DNA separation patterns from polyacrylamide gels gives problems for which no satisfactory solution has as yet been found. In an article published in 1984 (Church and Gilbert, 1984) a protocol for such a transfer to a nylon membrane filter is described within the framework of a method of directly determining the nucleotide sequence of genes in genomic DNA, but in practice it turned out to be extremely difficult to carry out the protocol successfully. The difficulty of realizing effective transfer is especially felt with denaturing gradient analysis. In denaturing gradient analysis, no agarose can be used, because this contains too coarse pores (poor separation) and is liquid at the electrophoresis temperature used (60° C.). Presumably, it is the very fine-mesh structure and the regular network structure of polyacrylamide which render the transfer of DNA, in particular double-stranded DNA, so difficult.

The inventors have made many attempts to transfer denaturing gradient separation patterns to membrane filters. For this they started from the protocol of Church and Gilbert, in which use is made of electrophoretic transfer (electroblotting). Although this protocol was found not to work for denaturing gradient separation patterns, the inventors have ultimately after all succeeded in making such variations as to produce a useful and reproducible protocol. The experience gained showed that it is not only the efficiency of transfer which plays a role, but so does the condition in which the DNA ultimately arrives on the filter (e.g., whether the fragments are single or double-stranded). This, in turn, is determinative of the efficiency of hybridization, which makes the ultimate result of the experiment dependent upon the probe used. We have found that the partly molten DNA contained in the polyacrylamide gel can be effectively transferred if the DNA is first further fragmented, for example, by irradiation with ultraviolet light (302 nm), and denatured, for example, by boiling in water.

Meanwhile, a second suitable protocol, although clearly more elaborate and more time consuming, has been developed by others. (Borresen et al., Mutation Research, 1988). In it, the electrophoretic separation is carried out in a mixture of agarose and polyacrylamide. The presence of the polyacrylamide permits denaturing gradient analysis. However, unlike normal polyacrylamide gels employing bis-acrylamide for cross-linking the long acrylamide chains, use is here made of a so-called reversible cross linker, namely, diallyltartardiamide. This means that, after electrophoretic separation, the cross-linkages can be broken by a treatment with periodic acid. As this does not affect the agarose, a pure agarose gel remains after the treatment and a number of washes. Transfer can now be effected by means of capillary blotting in accordance with normal procedures (Southern, 1975).

Recently the present inventors have suggested that two-dimensional gel electrophoresis, followed by hybridization analysis with repetitive DNA sequences as probes could be suitable for detecting transpositions in DNA with ageing (Vijg and Uitterlinden, 1987). A suitable protocol for the transfer of the separation pattern, however, is not given in that publication. Moreover, repetitive DNA sequences, in general, do not appear to be suitable for use as probes in a study directed to the linkage of genetic factors. On the contrary, in the preparation of probes for such work, repetitive sequences are the very thing one seeks to avoid as much as possible, because when used as a probe in Southern blot analysis, these sequences generate such a complex pattern of bands as to render the analysis of the genetic factors involved impossible.

A similar degree of complexity is found after two-dimensional analysis of total human genomic DNA. This gives clear "clustering" of restriction fragments in certain areas of the 2-D gel, both after staining with ethidium bromide (which visualizes all restriction fragments) and after hybridization using probes for repetitive DNA sequences.

Surprisingly it has now been found that such clustering does not occur when minisatellite-core sequences are used as a probe, and that then a two-dimensional pattern is obtained with a very good separation (see FIG. 6), in which the inheritance (see FIG. 9,10) of specific fragments (spots) can also be observed in a reproducible manner.

The analysis of 2-D patterns of HaeIII cleaved human genomic DNA with locus-specific VNTR probes (see FIG. 2 for the difference between a core probe and a locus-specific minisatellite probe) showed that both alleles of the locus migrate approximately to the same location in the denaturing gradient. It is our firm conviction that this is due to the relative GC richness of minisatellites (see FIG. 7A) relative to the adjoining regions. The stable GC-rich minisatellites of the restriction enzyme fragments we have created will be late to melt. This means that the flanking relatively AT-rich regions determine the electrophoretic behaviour of the restriction fragments in the gradient. As these flanking regions, unlike the minisatellites, are virtually non-polymorphic, the two alleles of a minisatellite locus will migrate to the same position in the gradient. This migratory behaviour was found to be independent of the size of the fragments concerned (ranging from 800 bp to 9500 bp) (see FIG. 8A and B). This provides the certainty that, in a complex 2-D spot pattern, both alleles of a given locus can always be found. In this, the 2-D method essentially differs from the use of the minisatellite core probes in genetic linkage studies, as suggested by Jeffreys et al., 1986. As hybridization analysis with other GC-rich repetitive sequences as probes (such as simple sequence motivs; Tautr and Renz, 1984) resulted in comparable high-resolution spot patterns (results not shown), it is reasonable to assume that GC-richness of the repetitive sequences is a condition for this. Indeed, we have shown that repetitive sequences with AT-rich regions result in a poor separation pattern (see e.g. the B1 repeat in FIG. 5, which is known to contain an AT-rich part).

The present invention accordingly provides a method of the above kind, which is characterized in that the electrophoretic separation of the DNA fragments generated is carried out in two dimensions on the basis of two independent criterions, the fragments being separated in one dimension on the basis of their length, and being separated in the other dimension on the basis of their base pair sequence, and by using as a probe in the hybridization analysis a labelled DNA or RNA molecule containing one or more cores of minisatellite sequences or other GC-rich repeats.

Thus the essence of the invention consists specifically in the use of core sequences of hyperpolymorphic minisatellites (or other GC-rich repeat sequences) for making linkage maps of an individual (not only Man, but also animals, such as, in particular, pedigree horses, pedigree dogs, etc., or plants with similar polymorphic sequences in their genomes) by means of electrophoretic separation in two dimensions of restriction fragments of the DNA of the individual, followed by transfer to a membrane and hybridization analysis.

The invention means:

(1) that, on the basis of the melting-out characteristics of DNA fragments containing a GC-rich repetitive sequence, two-dimensional individual-specific, high-resolution separation patterns can be obtained by means of hybridization analysis;

(2) that, on the basis of the above principle, the reliability of identity tests can be greatly improved;

(3) that, on the basis of the above principle, a large number of spots (alleles) can be followed simultaneously during their transmission in a family;

(4) that, on the basis of the above principle and information as to the position of the alleles studied in the genome, a so-called linkage map can be composed of an individual;

(5) that the accuracy of such linkage map is dependent upon the spacing between the marker loci in the genome, and hence on the number of spots that can be separated on one gel;

(6) that the above-described system can be used to directly link any heritable disease to a polymorphous marker;

(7) that the above-described system also lends itself to the association of genetic variation with the prevalence of diseases on the ground of linkage disequilibrium with one or more of the markers;

(8) that the above-described system is suitable for estimating risks after possible exposure to agents suspect of carcinogeneity;

(9) that the above described system is suitable for comparing complex populations of RNA molecules converted into DNA to which a GC-rich sequence has been attached;

(10) that the above system is excellently suitable for computerization by means of an advanced image analysis system coupled to a data file.

The above summary shows that the invention can be used for analyzing complex populations of nucleic acid molecules (DNA and RNA) in general, and specifically for identity tests (e.g., in forensic medicine as evidence for actorship, paternity and maternity), for mapping disease genes and association studies, and for the performance of mutagenicity tests. These uses will be illustrated hereinafter.

Identity tests: The application of the system according to this invention to enhance the reliability of identity tests is a first possibility. If it is realized that, in parenthood tests, in which 10 polymorphic alleles are involved in one gel, there is a chance of 1 to one million that an individual who is not the father yet has the 10 paternal alleles of the child, it is easily seen how, by means of the 2-D system as shown in FIG. 9, with which 54 paternal alleles have been found in one pass, a certainty can be obtained which is many times higher.

Mapping of disease genes: The mapping of disease genes is effected by means of linkage analysis. Linkage analysis comprises the determination of linked inheritance of polymorphic genetic markers with the disease genes. This is effected by determining within a family in which the transmission of the disease in question is precisely known, the different variants of a polymorphic marker (the alleles) in each member of the family. Subsequently, it is determined whether a given allele is always inherited together with the disease. If this is the case, the disease is said to be linked with the polymorphic marker in question and so should be located in close proximity to it. In order to map heritable diseases in this manner, a large number of polymorphic markers, spread over the genome with an average interspace of no more than about 10 million base pairs, should be analyzed (by means of Southern blot analysis) in the members of a family the heritable disease harbouring. If there is no indication whatsoever as regards the position where the disease gene in question is located, a total of at least 300 polymorphic markers regularly distributed throughout the genome should be considered (the total haploid genome is in fact $3.10^9$ base pairs long). For the simplest family consisting of a man, a woman and one child, this means 900 one-dimensional Southern analyses. In somewhat larger families, this may increase to as many as 20,000 Southern blots. Even if some 10 samples are analyzed on one blot, this is still 2000 blots. It is clear that this involves quite some time and material.

The present invention solves this problem by using certain characteristic properties of GC-rich repetitive sequences in denaturing gradient gels and linking these to the earlier-used electrophoretic size separation. The resulting 2-D separation patterns are characterized by a high resolution, as a consequence of which a great many VNTR's and similar polymorphic repetitive sequences can be analyzed. The application of the present invention in the detection of genetic defects and predispositions can basically be effected by two routes.

(a) The mixed use of previously characterized locus-specific probes. This finds application in particular in the cases in which there is advance information as to a given chromosome where the disease gene should be localized. In such a case, it is only necessary to use a limited set of probes. The great advantage over and above the prior approach is the huge gain in time that can be obtained by virtue of the fact that a large number of loci can be analyzed simultaneously, rather than one by one.

(b) The use of core probes detecting a large number of loci simultaneously. This application is excellently suitable for diseases where no information whatsoever is available as to the location and the number of genes involved in the disease. It is in particular with multifactorial diseases involving both a plurality of genes and environmental factors, such as rheumatoid arthritis, it is virtually impossible on the basis of the prior approach to get an insight into the location and identity of the genes involved. In fact, the number of Southern analyses needed to demonstrate linkage with a plurality of loci will increase tremendously, because a plurality of markers will have to be analyzed in a large number of families. In this kind of cases, sometimes as many as hundreds of individuals should be analyzed. Starting from the above 300 markers, this brings us close to 100,000 Southern blots.

By means of 2-D analysis, it is possible to analyze large parts of the genome simultaneously. Determinative of this is the number of alleles that can still be observed separate from each other.

Computer analysis by means of an image analysis system has shown that the experimentally realized separation patterns contain more than 700 spots. However, by simply using somewhat larger gels (and naturally using mixtures of a plurality of different probes) the total number of alleles to be detected can be considerably increased. If, for example, 1000 spots can be observed separate from each other, and 600 of these represent polymorphic alleles spread with regular intervals throughout the genome, the total genetic map of a human individual is already a fact. It is possible, by means of image analysis, to store the standard 2-D patterns of known polymorphic markers in the computer, whereafter the patterns of analyzed individuals can be compared with these in a simple manner. In this way, in principle, genes for all hereditary diseases can be detected very rapidly, provided DNA samples are available of families in which the disease has been transmitted in accordance with a well-defined pattern.

A total linkage map of an individual is extremely interesting for various reasons. One reason is that the position of a disease gene in the total genomic DNA can be determined with it very rapidly. This can simply be effected by generating a 2-D pattern of each member of the disease family with a mixture of about 300 polymorphic marker sequences (proportionally distributed throughout the genome) as a probe. Subsequently, it can be determined which of the circa 600 polymorphic alleles (spots) is inherited along with the disease. As a matter of fact, it is expected that members of the family which have the disease invariably exhibit a given spot which the individuals of that family not affected do not have. The spot in question can then be punched out of the gel and be cloned by means of routine procedures.

In this manner, markers can be obtained for all hereditary diseases. From these markers, the disease genes themselves can be traced, which renders it possible to make a detailed analysis of the biochemical defect. However, the markers can also be used for diagnostic purposes. In fact, within a family harbouring the disease, it can be established for each non-affected individual whether he or she is a carrier of the disease, and which offspring, if any will get the disease. At the present time, these tests are already rather simple to perform from about 10 ml blood or through amniotic fluid sampling (in the case of prenatal diagnostics), and there is every appearance that this will become a lot simpler yet on the basis of the polymerase chain reaction recently introduced. The crucial factor in each test, however, is the polymorphic marker. If, for example, a test kit will be marketed for the familiar form of the Alzheimer disease, it will contain, in addition to some chemicals for doing the test, the probe for the marker. The point is, therefore, to find a closest-proximity marker for each disease. It is this very detection of disease-linked markers which makes the technical system herein described so valuable.

Mutagenicity test: The testing of substances for carcinogenicity is of great importance in a society where ever more newly-synthesized chemicals make their appearance. Furthermore it is of importance for individuals who may have been exposed to carcinogens (or to radiation, as with disasters in nuclear power stations) to be examined for possible permanent adverse effects, such as an increased cancer risk or permanent damage to their genetic material. It has meanwhile become clear that both various forms of cancer and hereditary defects are caused by changes in the DNA. Mutagens (i.e., substances which change the base sequence of the DNA) are virtually always carcinogenic. Therefore many tests for carcinogenicity are based on the capability of the substance being tested to introduce mutations in the DNA. The most famous test is the Ames test in which bacteria are screened for mutations. As bacteria are not human beings, this test is not reliable as to 100%, and a diligent search is being made for methods comparable in price but more reliable in outcome. Generally speaking, tests with human cells are preferred. If a suspect substance gives no deviations in the DNA of human cells, this is much more reliable than a negative result in a bacterium. This is all the more the case if a great many genes are studied at the same time.

By means of 2-D analysis, not only can a great many genes be studied at the same time, but in particular those genes can be studied which can be assumed to be hypersensitive to mutagenic agents. The minisatellites are known not only to vary greatly between individuals, which suggests a high mutation frequency (Jeffreys et al., 1988), but also to undergo changes in, for example tumors (Thein et al., 1987). If an agent suspected of mutagenicity (and hence carcinogenicity) does not introduce changes in minisatellites, it may safely be assumed that it does not involve a risk for the genetic integrity of human beings exposed to it.

By analogy, 2-D analysis of minisatellites can be used for screening individuals exposed to carcinogens. By simply taking a blood sample and doing a 2-D analysis of the DNA contained in it, the genetic damage sustained by the person in question can be rapidly assessed by comparison to a previously taken sample from this individual.

The invention is illustrated in and by the following description of experiments conducted and with reference to the accompanying drawings.

FIG. 3 shows the autoradiogram of a Southern Blot Analysis of total genomic DNA isolated from postmortem brain tissue of five non-related individuals and cleaved with the restriction enzyme HaeIII. The probe used was the minisatellite consensus sequence 33.15.

Figure 1:
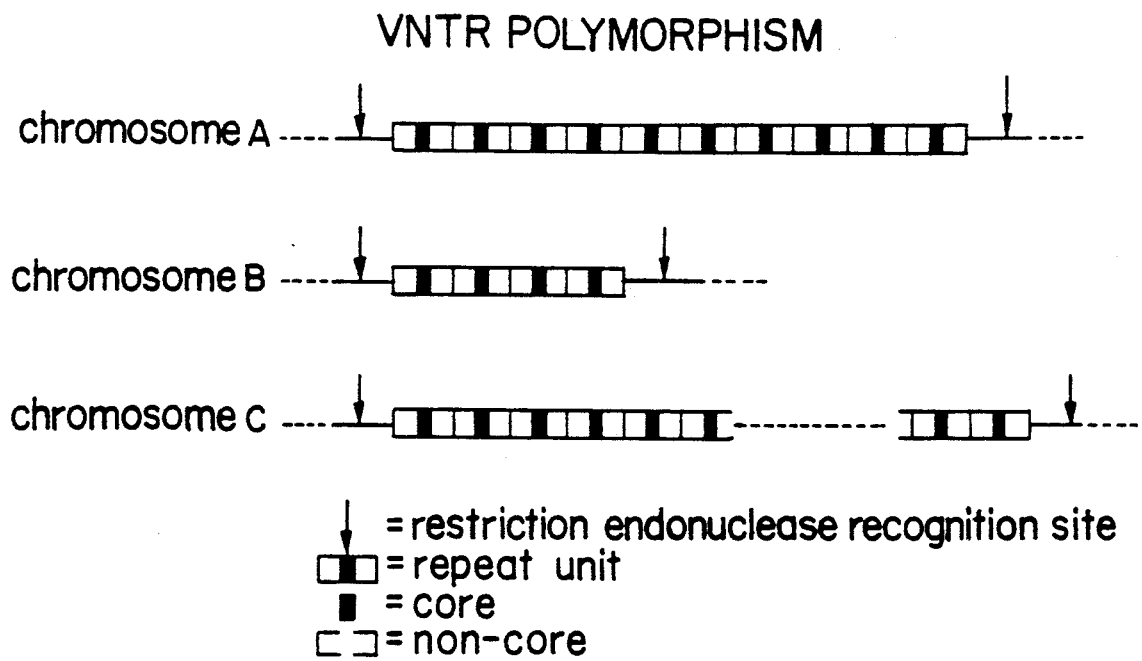
FIG. 1 shows three of a large number of possible variants of a minisatellite locus on a given chromosome. It is seen that the variants differ in the number of basic units of the minisatellite.
Figure 2:
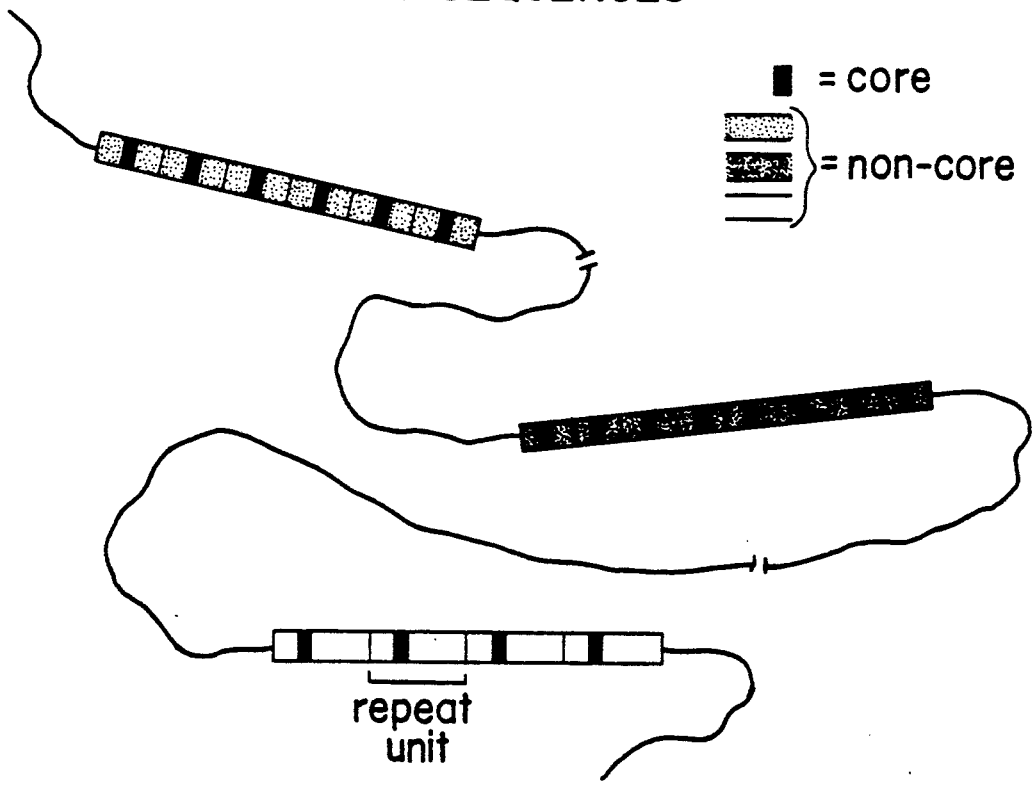
FIG. 2 shows the organization of different minisatellite loci in the genome. The differences between the loci are based on the so-called non-core portion of the basic unit of the minisatellite and the adjoining sequences.
Figure 4A:
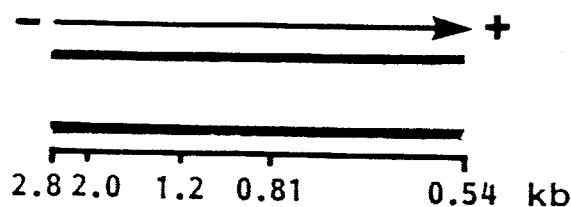
Figure 4B:
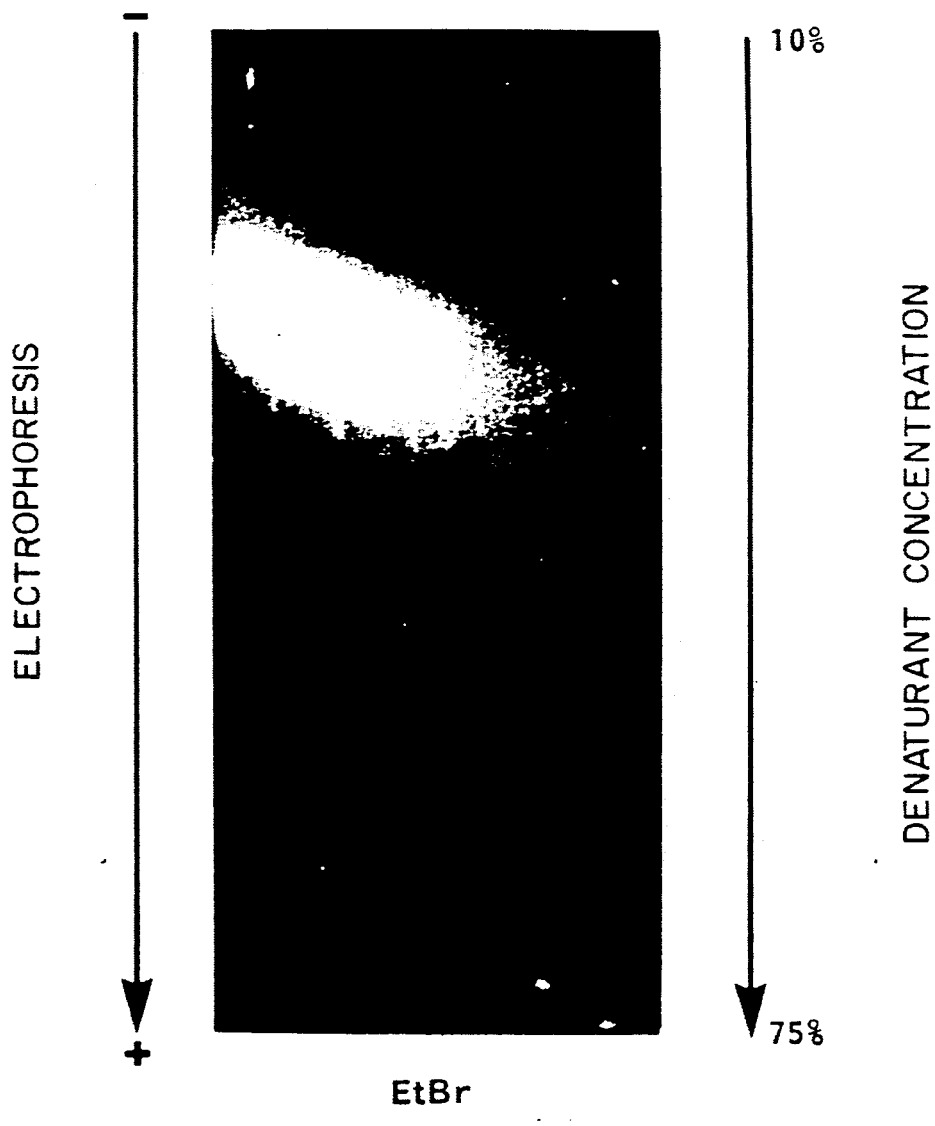

FIG. 4A and 4B shows a polyacrylamide gel stained with ethidium bromide, in which human genomic DNA cleaved with the restriction enzyme HaeIII has been separated in two dimensions. Size separation in the first dimension was effected in a neutral 6% polyacrylamide gel, whereafter the lane was cut out and applied breadth-wise to a polyacrylamide gel with a denaturing gradient, followed by sequence composition separation in the second dimension. This figure shows that the number of fragments generated by cutting the mammalian genome with the restriction enzyme HaeIII (about 1 million) is so large that they cannot be observed separate from each other. Another important conclusion that can be drawn from the results presented in FIG. 3 is the inadequacy of the separation criteria used; there is clearly clustering in two regions.

In order to obtain an insight into the structure of the total genome of an individual (and variations therein) after all, hybridization analysis with so-called repetitive DNA sequences as probes was investigated. Hybridization analysis is commonly effected by means of Southern hybridization (based on one-dimensional separation) using probes for unique genes. Possibly, hybridization of 2-D separation patterns with probes for families of repetitive DNA sequences regularly distributed throughout the genome could provide an interpretable pattern of spots.

However, a similar clustering to that found earlier for total genomic DNA (FIG. 4) was to be observed after hybridization of the gel pattern transferred to nylon filters with probes for the repetitive DNA sequence family B1 (FIG. 5). As this mouse repeat family (the human homologue is called Alu) is known to belong to the so-called dispersed repeat category (i.e., is regularly and randomly distributed throughout the genome), it was initially concluded that the low resolution, just as with total genomic DNA, was caused by inadequate separation in the second dimension.

FIG. 5 accordingly shows the autoradiogram obtained after hybridization analysis of a two-dimensional separation pattern of rat genomic DNA cut with HaeIII, using as a probe a B1 sequence, with which all B1 sequences spread throughout the genome can be detected in the 2-D pattern.

Later experiments proved, however, that the clustering observed was not due to inadequate separation in the second dimension, but was due to the choice of probe.

In addition to dispersed repeat families and tandem repeat satellites, there is a mixed form, namely, the so-called dispersed repeat minisatellites. These sequences consist of successive repeat units of 16-64 base pair each, and occur spread throughout the genome. Thus, for example, there is such a minisatellite at the 3' end of the cHa-ras proto-oncogene.

An important aspect of such minisatellites is their hyperpolymorphic character. Huge interindividual differences have been found as regards the number of repeat units in a given locus and between different loci. Minisatellites are organized, on the basis of a so-called core sequence, in families which are not homologous among themselves.

Jeffreys et al. showed that, by means of a core sequence as a probe, 10-15 minisatellite regions can be distinguished simultaneously by means of Southern analysis. They have used this finding in the identification of individuals; the hyperpolymorphic character of the minisatellite regions ensures individual differences in the position of the different bands on the Southern blot each representing a minisatellite region. It should be noted that the Southern analysis used by Jeffreys is capable of distinguishing only 10-15 of the longest minisatellite-containing restriction fragments (see FIG. 3).

Another important use of the hyperpolymorphic minisatellite sequences is as markers in genetic linkage analyses of disease genes. Their suitability for linkage analyses is determined by their hyperpolymorphic character and the fact that a minisatellite, as a whole, unlike the core sequence, does not exhibit cross hybridization with other minisatellite sequences elsewhere in the genome.

As noted before, in the initial use of minisatellites in the identification of individuals, their repetitive character was an important advantage, whereas for linkage analysis this very property is undesirable. The use of core probes in linkage analysis is not sufficiently informative, because only a very limited portion of the alleles can be visualized, and there is never the guarantee that the maternal and the paternal allele can be observed simultaneously and separate from each other (one of the two, for example, may be located in the poorly separated smear at the bottom of the gel; see, for example FIG. 3).

Figure 6:
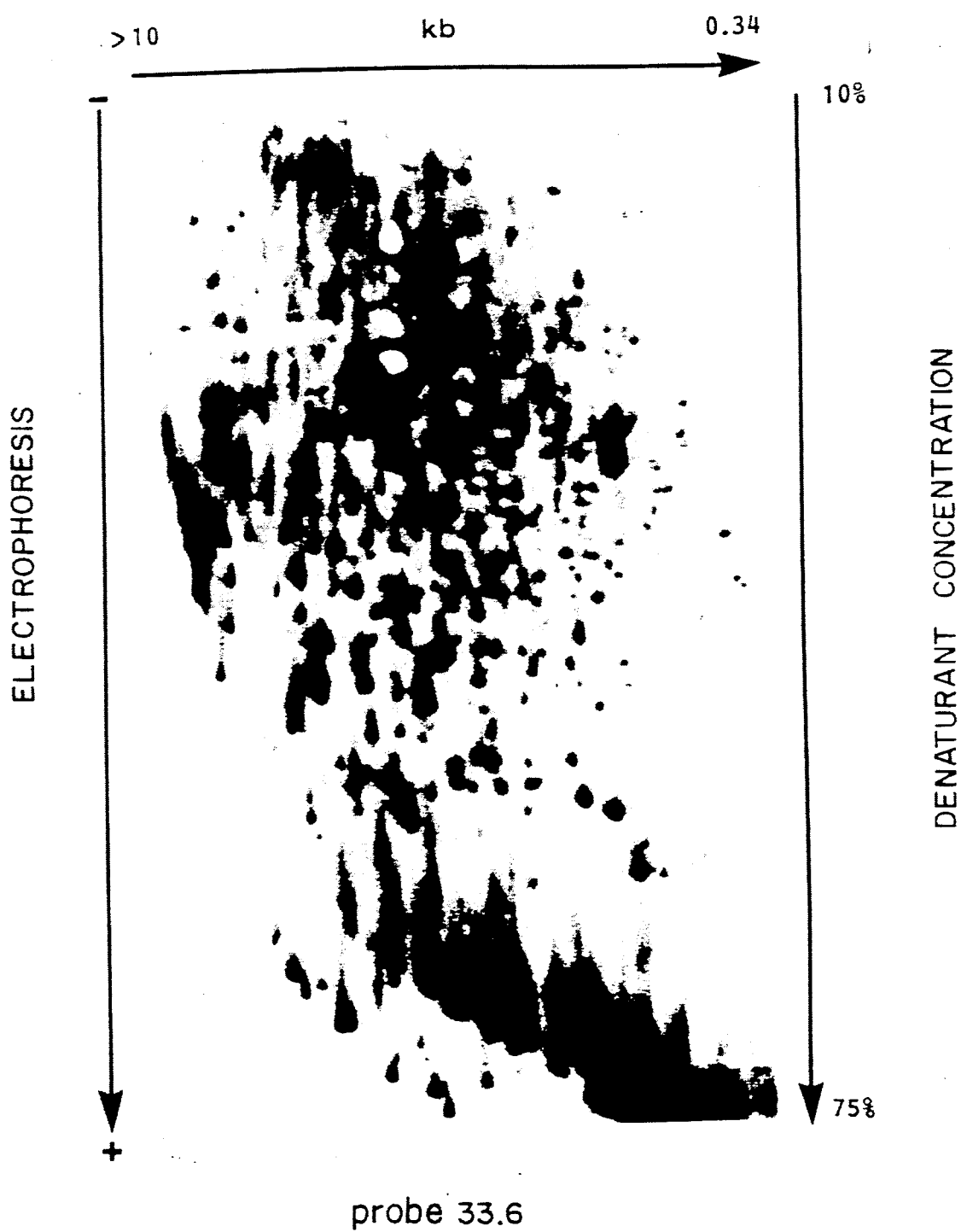

It was decided to make an attempt to use a minisatellite core sequence as a probe in the hybridization analysis of 2-D separation patterns. It was surprisingly found that, unlike the B1 dispersed repeat family tested before, and already after the first attempt, this gave an excellent separation in the second dimension and a spot pattern distributed virtually optimally throughout the entire gel (FIG. 6). FIG. 6 shows an autoradiogram obtained after the hybridization of a two-dimensional separation pattern of human genomic DNA cut with HaeIII, using as a probe the minisatellite core sequence 33.6. FIG. 7A gives a survey of some minisatellite core sequences synthesized within the framework of this invention. In addition, still other core sequences, rich in GC and not rich in GC, have been used, namely so-called simple sequences, (CAG)n and (GT)n, as well as a probe for the B1 repeat family.

FIG. 7B is a flow sheet of the preparation and radioactive labelling of the VNTR core sequences as used in this invention.

Figure 7C:
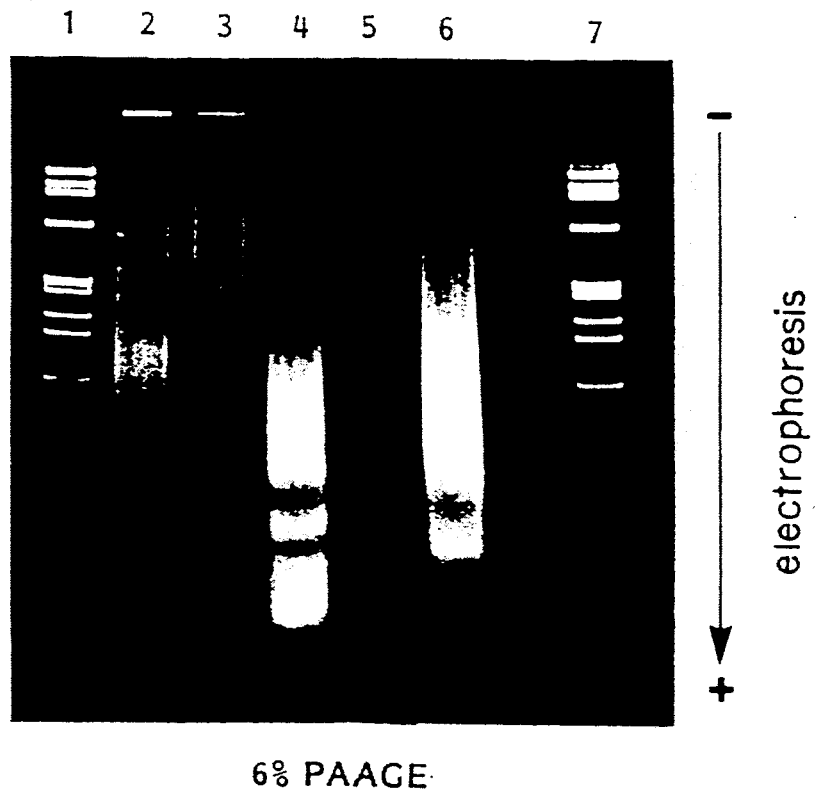

FIG. 7C shows the result of polyacrylamide gel electrophoresis of VNTR core probes synthesized by us. The figure shows that the probes consist of polymers of the core sequence ranging in length from 11 to about 2500 base pairs.

Figure 8A:
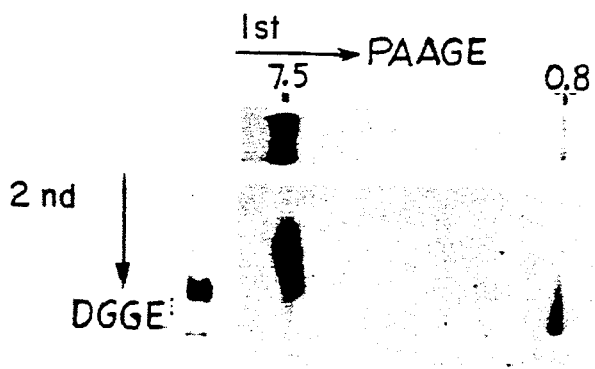

An indication as to why it is this very repeat family which gives a regular separation pattern in the denaturing gradient was obtained by two-dimensional analysis of a VNTR locus by means of a locus-specific probe (see FIG. 8A). DNA isolated from individual 24 was cut with HaeIII and separated in two dimensions. The figure shows the autoradiogram obtained after hybridization analysis with the locus-specific probe p λG3. For clarity, one-dimensional separations of the same DNA's are shown in neutral polyacrylamide (1st PAAGE) and in a denaturing gradient gel (2nd DGGE). The pattern of individual 24 clearly shows that both alleles (7.5 and 0.8 kb) migrate to approximately the same position in the denaturing gradient, in spite of their huge difference in size. Similar observations have been made with DNA's of other individuals.

Figure 8B:
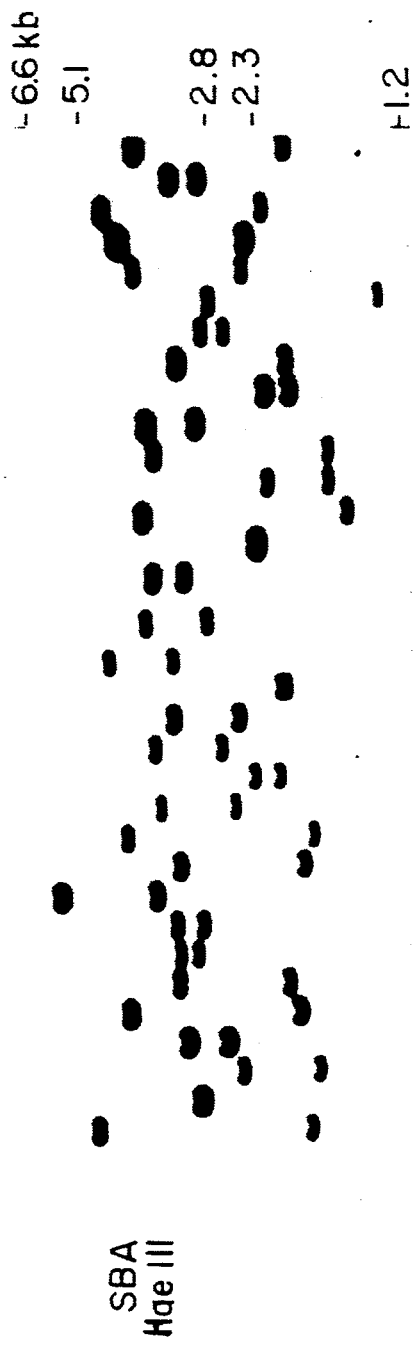
Figure 8C:
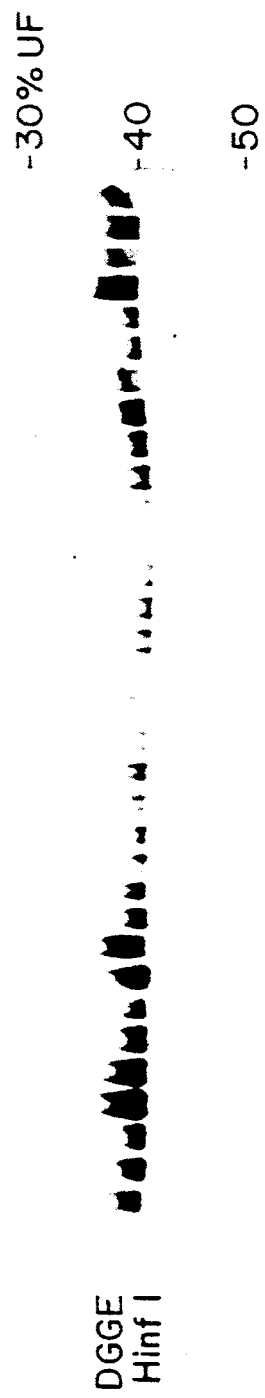

FIGS. 8B–C shows the results of agarose gel electrophoresis and denaturing gradient gel electrophoresis (in one dimension) of cut DNA from 34 different individuals. The figure shows the autoradiograms obtained after hybridization with the locus-specific VNTR probe pYNH 24. It is clearly shown that all alleles in the denaturing gradient migrate to one position in the gel (the isotherm), whereas the various alleles in the agarose gel migrate to different places on the basis of their length.

In order to determine whether the resulting separation patterns had a sufficiently high resolution to follow segregation of alleles, 2-D analyses were performed in a family consisting of father, mother, and a son.

Figure 9A:
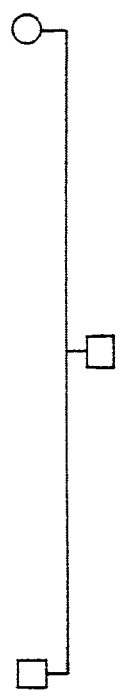
Figure 9B:
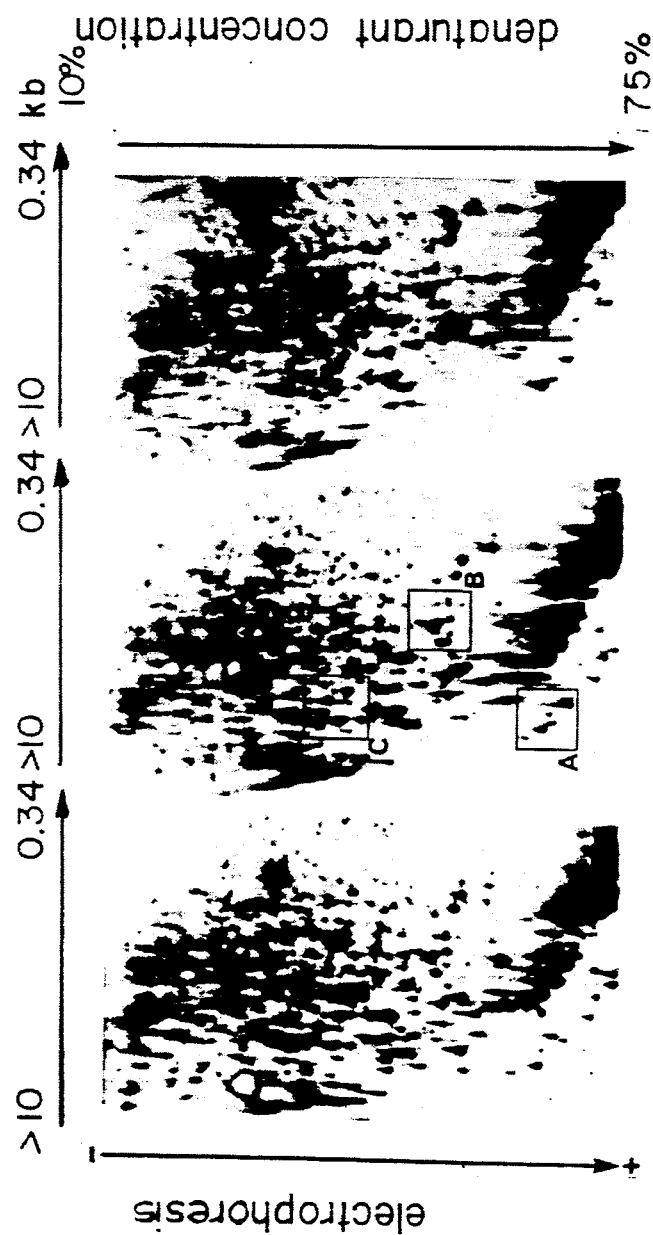

FIGS. 9A–B shows an autoradiogram obtained after the hybridization analysis of a two-dimensional separation pattern of human genomic DNA cut with HaeIII, using as a probe the minisatellite core sequence 33.6. Three DNA samples from a father, a mother and their son have here been electrophorsed in one gel.

With the naked eye, about 600 spots can be distinguished per individual (computer analysis later showed that there are some more), 150 of which are polymorphic (different in father and mother). Of these, 105 are segregating (52 paternal and 53 maternal) and 45 are not to be found in the son's pattern. This last is caused because, of a heterozygous locus, such as a minisatellite, all alleles will never be transferred to one child.

FIGS. 10A–D shows further details of regions designated A, B and C in FIG. 9. Some polymorphisms are shown in detail (circle: maternal allele; square: paternal allele).

The great importance of the experiment the results of which are shown in FIG. 9 is the fact that all alleles belonging to the minisatellire family in question can be found back. Although, theoretically, under a given spot there may be another, quite different one which happens to be both of the same size and of the same melting characteristics, this may be regarded, unlike the situation in a classical Southern blot analysis, as extremely unlikely. The two-dimensional spot patterns shown in FIG. 9 can therefore be regarded as genomic maps of individuals, in which connection it should be noted that they do not acquire their value as linkage maps until after identification of the individual spots. This identification is at present well under way by means of the unique minisatellite probes and classical Southern Blot Hybridization analysis. It is to be expected, therefore, that, in the near future, the fragments visualized in one gel can be identified in one pass through a data file. The total gene map of a human individual is then a fact.

In the experiments conducted, the following materials and methods were used.

DNA isolation and restriction enzyme digestion:

For making 2-D patterns as described above, in principle any tissue can be used as a source for the DNA. Cultured cells are also suitable. Generally speaking, use can be made of standard DNA isolation procedures. In the experiments as described above, DNA was isolated from brain tissue from different individuals, and from blood, also of different individuals. The following procedure was followed in the isolation of DNA from brain tissue. Deep frozen postmortem cerebellum was fragmented and incubated overnight at 65° C. in 2 volumes of a solution containing 100 mM Tris, pH 7.5, 250 mM Na-EDTA, 1% sodium dodecyl sulphate (SDS) and 100μg/ml proteinase K (BRL). After the admixture of 1 volume of 8M potassium acetate, the solution was kept on ice for 2 hours and then extracted with 1 volume of chloroform. The DNA was obtained from the aqueous phase by ethanol precipitation and then dissolved in water. The DNA's from blood were obtained from Dr. E. Bakker (Department of Antropogenetics, University of Leiden) where they were isolated by means of a standard procedure. DNA (10μg) was cut with the restriction enzymes endonuclease HaeIII or HinfI (BRL) under conditions as described by the manufacturer.

Electrophoretic separation

Two-dimensional separation of 10μg DNA restriction fragments was carried out in polyacrylamide gels (acrylamide:bisacrylamide=37:1). The first dimension was done in a neutral gel at 50° C. for 2 hours at 250 V in 1×TAE (40 mM Tris, pH 7.4, 20 mM sodiumacetate, 1 mM sodium EDTA). The 1-D separation patterns were visualized by means of staining (in the dark) with ethidium bromide (0.1 μg/ml) for 10 minutes, followed by decolourization in deionized water for at least 30 minutes. The 0.54–2.8 kb region was cut out of the lane and applied transversely to a second 6% polyacrylamide gel, which contained a 10–75% linear concentration gradient of denaturant (100% denaturant=7.0 M urea, 40% formamide) parallel to the direction of electrophoresis. These gels were cast by mixing the boundary solutions in a linear gradient former, using a peristaltic pump. For this second dimension, in addition to the 20 cm wide standard apparatus, use was often made of one 30 cm wide, which accommodates lanes side by side. After electrophoresis for 12 hours at 225 V and at 60° C., the gel was stained with ethidium bromide and decolourized to visualize the separation pattern.

Transfer of the separation patterns to membrane filters

The two-dimensional separation patterns were first fragmented by irradiating the gel with 302 nm ultraviolet light (UV) for 4 minutes, which turned out to be optimal. Prior to the transfer, the gel was boiled for 5 minutes in 1×TBE (89 mM Tris, 89 mM boric acid, 2 mM sodium EDTA) and then transferred to 1×TBE. Transfer to nylon membrane (Nytran 13N, Schleicher and Schuell or Zetabind, BioRad) was accomplished by electroblotting at 400 mA (12–28 V) at 15° C. in an electroblotting apparatus using graphite plates. Electroblotting was effected over two periods of 45 minutes between 10 sheets of Whattman 3MM paper soaked in fresh 1×TBE (changed between the two electroblotting periods). After transfer, the filter was rinsed in 2×SSC (1×SSC=150 mM NaCl, 15 mM sodium citrate), dried in the air, heated at 80° C. in a furnace for 1 hour, and irradiated with 302 nm UV for 45 seconds.

Preparation and radioactive labelling of the probe

The probe was prepared by individually kinating two partially complementary and overlapping oligonucoleotides (see FIG. 7). One such pair represents a minisatellite core sequence. The sequence used was core sequence 33.6 (5'-AGGGCTGGAGG-3'). After kination, the two oligo's were mixed and annealed at 57° C. for 1 hour, followed by ligation by standard procedures (Maniatis et al., 1982). The synthetic probe thus prepared had an average length of 500 base pairs or more (see FIG. 7C). 50 ng of the ligation products was labelled with α-$^{32}$P-dCTP, either by means of the random primed oligo labelling method (Boehringer) or by selfpriming after boiling for 5 minutes and reannealing in the presence of 1 unit of Klenow enzyme (Boehringer), 2 μM dNTP, 50 mM Tris, pH 7.2, 10 mM MgCl$_2$. Specific activities of 3 to $8 \times 10^8$ c.p.m./μg were achieved.

Hybridization analysis

The filter was prehybridized in 5×SSC, 20 mM sodium phosphate, pH 7.2, 1% SDS, 1 mM sodium EDTA, 50 μg/ml heparin at 65° C. for 2 hours. After the addition of the denatured probe in a concentration of $1 \times 10^6$ c.p.m./ml, hybridization followed at 65° C. for 12 hours. The filter was then washed in 2.5×SSC, 0.1% SDS, thrice at room temperature for 5 minutes and thrice at 65° C. for 20 minutes. Autoradiography was at −80° C. with Kodak XAR-5 film between fine intensifying screens (Kodak) for 12–48 hours.

LITERATURE REFERENCES

1. EP-A-0186271
2. Borresen et al., (1988) Mutation Research 202, 77–83.
3. Botstein et al., (1984) Am.J.Hum.Genet.32, 314–331
4. Church and Gilbert (1984) Proc.Natl.Acad.Sc. USA 81, 1991–1995
5. Donis-Keller et al. (1987) Cell 51, 319–337
6. Fischer and Lerman (1979) Cell 16, 191–200
7. Gusella (1986) Ann. Rev.Biochem. 55, 831–854
8. Jeffreys et al. (1985a) Nature 314, 67–73
9. Jeffreys et al. (1985b) Nature 316, 76–79
10. Jeffreys et al. (1986) Am. J.Hum.Genet. 39, 11–24
11 Jeffreys et al. (1988) Nature 332, 278–281.
12. Maniatis et al., (1982) Molecular Cloning; A laboratory Manual.Cold Spring Harbor Laboratory Press, New York.
13. Nakamura et al., (1987) Science 235, 1616–1622
14. Nakamura et al., (1988) Genomics 2, 302–309
15. Po et al., (1987) Nucleic Acids Res.15, 5069–5083
16. Southern (1975) J.Mol.Biol. 98, 503–517
17. Tautz and Renz (1984) Nucleic Acids Res.12, 4127–4138
18. Thein et al., (1987) Br.J.Cancer 55, 353–356
19. Vijg and Uitterlinden (1987) Mech.Ageing Dev. 41, 47–63

We claim:

1. A method of detecting genetic variation by fragmenting double-stranded DNA by means of one or more restriction enzymes, separating the resulting fragments by electrophoresis, transferring the resulting separation pattern to a membrane filter, hybridizing thereon under DNA-denaturing conditions with a labelled DNA or RNA probe, and visualizing the label, characterized in that the electrophoretic separation of the DNA fragments generated is carried out in two dimensions on the basis of two independent criteria, the fragments being separated in one dimension on the basis of their length and being separated in the other dimension on the basis of their base pair sequence, and in that the probe used in the hybridization analysis is a labelled DNA or RNA molecule containing one or more cores of minisatellite sequences or other GC-rich repeats.

2. A method as claimed in claim 1, characterized in that the DNA fragments generated are first separated on the basis of their length in a neutral polyacrylamide gel, and subsequently, in the second dimension, are separated on the basis of their base pair sequence in a polyacrylamide gel having an increasing concentration gradient of a DNA denaturant parallel to the direction of electrophoresis.

3. A method as claimed in claim 2, characterized in that the electrophoretic separation on the basis of length is carried out at a temperature of between 45° and 55° C, and the electrophoretic separation on the basis of base pair sequence is carried out at a temperature of between 55° and 65° C.

4. A method as claimed in claim 2, characterized in that the separation pattern obtained after the two-dimensional electrophoresis is transferred to a membrane filter by electroblotting, and that prior to said transfer the separation pattern is fragmented by irradiation and further denatured by heating.

5. A method as claimed in claim 1, characterized by using as the membrane filter a nylon membrane or comparable material.

6. A method as claimed in claim 1, characterized by using as a probe a DNA molecule containing one or more GC-rich cores for repeat sequences, such as minisatellites or simple sequences or a mixture of locus-specific probes.

7. A method as claimed in claim 1, characterized in that the DNA fragments generated are derived from specially constructed cDNA libraries, in which GC-rich sequence have been attached to cDNA molecules prepared from complex RNA populations (such as total RNA from organs, tissues or cells).

8. A method as claimed in claim 1, characterized by using a probe labelled with a radioactive isotope, for example $^{32}$P or non-radioactive label, such as biotin.

9. A kit for use in the method as claimed in claim 1, comprising a labelled probe containing one or more cores of minisatellite sequences or other GC-rich repeats and material for two-dimensional electrophoresis containing a geld with concentration gradient of a DNA denaturant, suitable for separation of DNA fragments on the basis of their basie pair sequence.

* * * * *